United States Patent [19]
Hofmann

[11] Patent Number: 5,079,240
[45] Date of Patent: Jan. 7, 1992

[54] SYNTHETIC CONJUGATED BILE ACID AND METHOD OF USE THEREOF

[75] Inventor: Alan F. Hofmann, La Jolla, Calif.

[73] Assignee: The Regents of the University of California, Oakland, Calif.

[21] Appl. No.: 493,902

[22] Filed: Mar. 15, 1990

[51] Int. Cl.$^5$ .............................................. A61K 31/56
[52] U.S. Cl. .................................. 514/182; 514/867; 514/877
[58] Field of Search ................. 514/182; 552/549–553

[56] References Cited

U.S. PATENT DOCUMENTS

| | | | |
|---|---|---|---|
| 3,846,411 | 11/1974 | Widauer et al. | 552/552 |
| 3,852,440 | 12/1974 | Weigand | 514/170 |
| 3,859,437 | 1/1975 | Weigand | 514/177 |
| 3,910,888 | 10/1975 | Widauer et al. | 552/552 |
| 4,171,352 | 10/1979 | Wolgemuth et al. | 424/9 |
| 4,172,085 | 10/1979 | Monks et al. | 552/553 |
| 4,202,876 | 5/1980 | Monks et al. | 424/9 |
| 4,207,308 | 6/1980 | Spenney | 514/169 |
| 4,220,598 | 9/1980 | Hixson et al. | 552/552 |
| 4,263,272 | 4/1981 | Frigerio | 424/486 |
| 4,264,514 | 4/1981 | Hixson et al. | 552/552 |
| 4,264,583 | 4/1981 | Jandacek | 514/182 |
| 4,388,241 | 6/1983 | Monks | 552/553 |
| 4,565,810 | 1/1986 | Castagnola et al. | 514/182 |
| 4,579,730 | 4/1986 | Kidron et al. | 424/465 |
| 4,593,073 | 6/1986 | St. Pierre et al. | 424/78 |
| 4,648,995 | 3/1987 | Mosbach et al. | 552/550 |
| 4,681,876 | 7/1987 | Marples et al. | 514/182 |
| 4,826,679 | 5/1989 | Roy | 514/851 |
| 4,957,910 | 9/1990 | Sutton et al. | 514/182 |

FOREIGN PATENT DOCUMENTS

| | | |
|---|---|---|
| 1618265 | 3/1971 | Fed. Rep. of Germany . |
| 3723940 | 1/1989 | Fed. Rep. of Germany . |

OTHER PUBLICATIONS

Nair et al., CA 73: 52415r (1970).
Miyairi et al., CA 101: 106870c (1984).
Batta et al., CA 102: 20222b (1984).
Heuman, CA 111: 93142w (1989).
Schmassmann et al., CA 112: 116237t (1990).

*Primary Examiner*—Shep K. Rose
*Attorney, Agent, or Firm*—Brown, Martin Haller & McClain

[57] ABSTRACT

A method is described for the replacement of bile acid in the biliary tract during conditions of bile acid deficiency which comprises administering an effective amount of a synthetic bile acid comprising the reaction product of a natural bile acid and an N-alkyl amino acid. A critical element of the invention is the presence of the N-methyl amino acid as the conjugating moiety for the synthetic bile acid. Such does not occur in nature, and is a key factor in the ability of the compounds of this invention to be efficacious in the treatment method of the invention.

Also described is a bile acid replacement composition which comprises the reaction product of a natural bile acid and an N-alkyl amino acid. The N-alkyl amino acid is an N-alkyl glycine, more preferably N-methyl glycine; the natural bile acid is cholic acid; and in the exemplified embodiment the compound is the N-acyl reaction product of N-methyl glycine and cholic acid, i.e., cholylsarcosine.

Potential clinical uses of the compounds of this invention as natural bile acid replacements include use when natural bile acid secretion into the small intestine is decreased or when normally secreted bile acids are deconjugated by bacterial overgrowth.

34 Claims, 3 Drawing Sheets

SYNTHETIC CONJUGATED BILE ACID AND METHOD OF USE THEREOF

STATEMENT OF GOVERNMENT RIGHTS

This invention was made with government support under Grant/Contract Nos. DK 21506, DK 32130, and Sub-Contract Nos. 5 ROI AM 32130-04 and 2 ROI DK 32130-06, awarded by the National Institutes of Health. The Government has certain rights in this invention.

BACKGROUND OF THE INVENTION

1. Field of the Invention

The invention herein related to the treatment of bile acid deficiency states and to improvement of the composition of the circulating bile acids. It also relates to synthetic bile acids for such uses.

2. Background and Prior Art

Natural bile acids are the water-soluble end products of cholesterol metabolism in most mammals. Bile acids, in the form of their anions, also function as biological surfactants which form mixed micelles and thereby promote lipid transport.

After their biosynthesis from cholesterol, natural bile acids are conjugated with the amino groups of glycine or taurine (in N-acyl linkage) by hepatic enzymes; the resultant conjugated bile acids are secreted into bile. In bile, bile acids form mixed micelles with phospholipid and cholesterol, solubilizing cholesterol and permitting its excretion into the small intestine from which it is poorly absorbed. In the small intestine, bile acids form mixed micelles with monoglycerides and fatty acids—the products of digestion of dietary triglyceride—accelerating their absorption. The solubilization of fat soluble vitamins in mixed micelles is essential for their absorption. Conjugated bile acids are not hydrolyzed during their transit down the small intestine, since the amide bond between the carboxyl group of the bile acid and the amino group of the glycine or taurine is resistant to pancreatic carboxypeptidases.

Bile acids are actively and efficiently absorbed by the terminal small intestine. Their efficient absorption leads to a large recirculating mass of bile acids, called the "bile acid pool."

For bile acids to form mixed micelles with lipids such as fatty acids and monoglycerides (the digestive products of dietary triglyceride), bile acids must be above a critical concentration, termed the critical micellization concentration ("CMC"). When bile acids are present at a concentration below the CMC, defective solubilization of lipolytic products and 17 fat soluble vitamins occurs, causing their malabsorption. Bile acid deficiency occurs when the ileal absorption of bile acids is impaired because of ileal dysfunction (such as might occur in inflammatory disease of the ileum, e.g. Crohn's disease) or resection of the ileum. Bile acid deficiency can also occur because of lack of secretion of bile acids into the proximal small intestine—either because of obstruction of the biliary tract or diversion of the biliary tract to the outside (biliary fistula). Bile acid deficiency can also occur in the small intestine when there is bacterial overgrowth; bacteria deconjugate the bile acids forming the parent compounds, unconjugated bile acids. These unconjugated bile acids, being weaker acids and more lipophilic molecules, can be absorbed rapidly (passively) when formed or may precipitate from solution as the insoluble protonated acid.

There is thus a need to replace bile acids in conditions of bile acid deficiency to restore the absorption of fat and fat-soluble vitamins to normal. There is also a potential need to replace bile acids in biliary fistula patients who require lipid-soluble drugs, for example, liver transplant patients who require cyclosporin.

Previous attempts to replace bile acids have used either a pure conjugated bile acid such as taurocholate (cholyltaurine), an unconjugated bile acid such as ursodeoxycholic acid, or desiccated ox or sheep bile. A second approach has 17 been to use a synthetic nonionic detergent.

None of these have proved very satisfactory. For any bile salt, the amount to be administered must be large—since the amount of bile salts secreted per meal is 4-6 grams.

If unconjugated bile acids are administered, they are insoluble at intestinal pH, and must be absorbed, conjugated by the liver and resecreted into bile (in conjugated form) before they are effective. The major problem with replacement therapy using animal bile preparations or conjugates of cholic acid is that administered natural bile samples contain dihydroxy bile acids which induce the colon to secrete, that is, they are cathartic. In addition, cholic acid derivatives are biotransformed to deoxycholic acid in the colon by bacterial 7-dehydroxylation, and the resultant deoxycholic acid is a potent secretory agent. Thus, when a pure conjugated derivative of cholic acid or sheep or ox bile is administered, even if steatorrhea is improved, diarrhea is worsened; the patient does not feel better. The one exception to this is the patient with an ileostomy. Here, administered bile acids can enhance the absorption of fat, yet not induce colonic secretion, because there is no colon.

Additional background of the present discovery includes studies of the physicochemical events in fat digestion and absorption, as well as the structural requirements for the induction of colonic secretion by bile acids. It has been shown that the nature of the amino acid present in bile acid conjugates determines the susceptibility of bile acid conjugates to bacterial deconjugation. For example, d-amino acid conjugates are not hydrolyzed by cholylglycine hydrolase, N-methyl glycine (sarcosine) conjugates of a number of common bile acids are not hydrolyzed by cholylglycine hydrolase in vivo, the sarcosine conjugates of ursodeoxycholic acid are not hydrolyzed in vivo. and cholylsarcosine is not hydrolyzed during enterohepatic cycling in rodent species. The significance of the resistance to hydrolysis is that the unhydrolyzed compound does not undergo 7-hydroxylation, and therefore is not biotransformed by bacterial enzymes into a secretory agent.

SUMMARY OF THE INVENTION

In one aspect, the invention herein is a method for the replacement of bile acid in the biliary tract during conditions of bile acid deficiency which comprises administering an effective amount of a synthetic bile acid comprising the non-deconjugatable reaction product of a natural bile acid and an N-alkyl amino acid or acid analogue. A critical element of the invention is the modification of the side chain of the bile acid to impart to the compound the ability to resist bacterial hydrolysis and thereby resist bacterial deconjugation. Such changes include but are not limited to conjugation with an uncommon amino acid or amino acid analogue such as a d-amino acid, β-analine or n-acetyl glycine; replacement of the peptide bond by a hydrolysis resistant bond such as an ether bond or an "inverse" peptide bond in which the amino group is on the bile acid and the carboxyl group is on the amino acid; or replacement by an amino acid containing bulky groups close to the peptide bond which inhibit hydrolysis. Most preferred is the presence of an N-alkyl amino acid or analogue as the conjugating moiety for the synthetic bile acid. Such does not occur in nature, and results in the ability of the compounds of this invention to be efficacious in the treatment method of the invention.

Thus, in another aspect, the invention herein is a bile acid replacement composition which comprises the nondeconjugatable reaction product of a natural bile acid and an N-alkyl amino acid or acid analogue.

In preferred embodiments, the N-alkyl amino acid or acid analogue is an N-alkyl glycine, more preferably N-methyl glycine; the natural bile acid is cholic acid; and in the exemplified embodiment the conjugated reaction compound is the N-acyl reaction product of N-methyl glycine and cholic acid, i.e., cholyl-sarcosine.

Potential clinical uses of the compounds of this invention as bile acid replacements include use when natural bile acid secretion into the small intestine is decreased or when normally secreted bile acids are deconjugated by bacterial overgrowth. Decreased bile acid secretion is found in patients with ileal resection or dysfunction or with biliary fistula, while increased bacterial deconjugation occurs in patients with a blind loop syndrome.

BRIEF DESCRIPTION OF THE DRAWINGS

The Figures of the drawings are graphs presenting experimental data illustrating aspects of the invention.

DETAILED DESCRIPTION AND PREFERRED EMBODIMENTS

Figure 1:
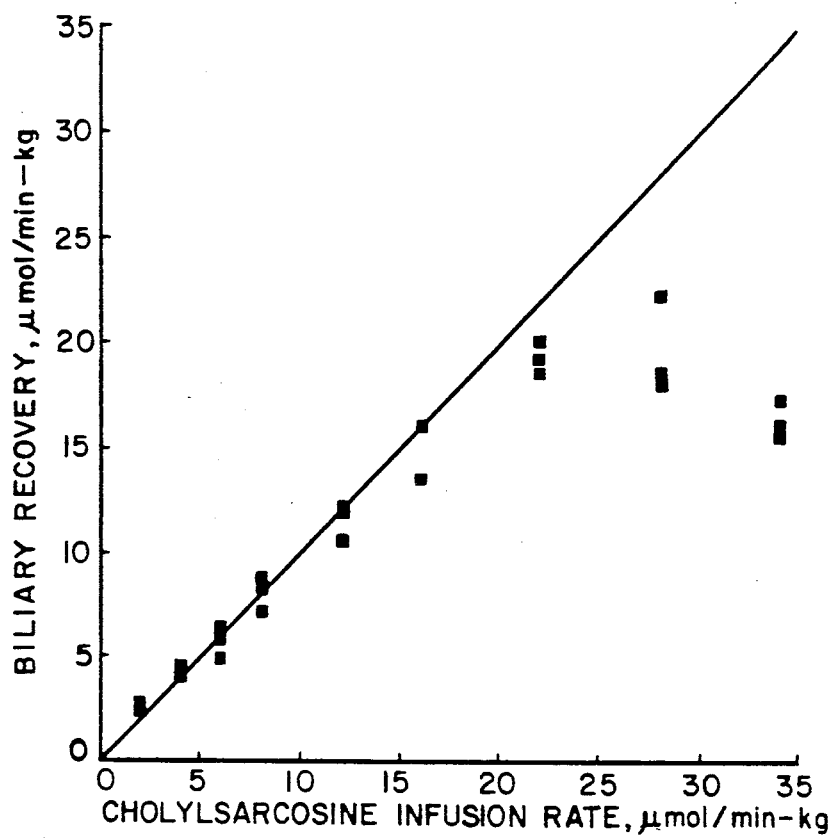
FIG. 1 is a graph showing hepatic transport of cholylsarcosine in the anesthetized biliary fistula rat.

The invention herein involves the use in appropriate clinical conditions of effective amounts of a synthetic conjugated bile acid prepared by coupling specific natural bile acids in N-acyl linkage to specific N-alkyl amino acids. In the preferred embodiment, the synthetic conjugated bile acid is cholylsarcosine, formed by the N-acyl reaction of cholic acid and sarcosine (N-methyl glycine). The resultant synthetic compounds, when ingested orally, will dissolve in the small intestine but are not deconjugated and can thus function as a natural bile acid replacement in clinical conditions of natural bile acid deficiency, such as ileal dysfunction. In healthy individuals, the compounds will be absorbed from the ileum and will increase the hydrophilicity of the circulating bile acid pool. Increasing the hydrophilicity of the bile acid pool, when induced by other bile acids such as ursodeoxycholic acid, has been associated with improvement in symptoms and liver tests in patients with chronic cholestatic liver disease.

In order to identify suitable compounds for use in the method of this invention, it is necessary to recognize the nature of the medical and physiological conditions to which the method is applicable. Bile acid replacement is analogous to pancreatic enzyme replacement, which has been the standard treatment for pancreatic exocrine insufficiency. Therefore, the compound to be administered must have the following properties:

(1) It must have the properties of the natural bile acids, including reasonably low critical micellization concentration (CMC), excellent water solubility, resistance to precipitation by $Ca^{++}$, excellent solubilization of fatty acids and monoglycerides, and promotion of lipid absorption in bile acid deficiency states.

(2) It must also have resistance to bacterial degradation to biotransformation products which induce colonic secretion.

(3) In addition, it must have an absence of significant toxicity.

(4) It must remain insoluble in the stomach so as not to cause damage to the gastric muscoa. It must be in dispersed form in the gastric contents, so as to empty with the meal. In this regard, enteric coated tablets are retained in the stomach and are not suitable.

It would also be very desirable for it to have low cost and known pharmacology. The compounds of this invention meet these criteria.

The class of compounds which are useful herein are those synthetic conjugated bile acids which are formed by the reaction of natural bile acids in N-acyl linkage with N-alkyl amino acids. The number of such reaction products which meet the above criteria is believed to be small, and there are a number of materials which we have identified which, while being reaction products of such bile acids and amino acids, do not satisfactorily substitute for natural bile acids since they become deconjugated. Compounds useful herein will be those in which the side chain of the bile acid is modified to impart to the compound the ability to resist bacterial hydrolysis and thereby resist bacterial deconjugation. Such changes include but are not limited to conjugation with an uncommon amino acid or amino acid analogue such as a d-amino acid, $\beta$-analine or n-acetyl glycine; replacement of the peptide bond by a hydrolysis resistant bond such as an ether bond or an "inverse" peptide bond in which the amino group is on the bile acid and the carboxyl group is on the amino acid; or replacement by an amino acid containing bulky groups close to the peptide bond which inhibit hydrolysis. In view of this description, it will be a simple matter of routine testing for those skilled in the art to identify those compounds which, while not expressly identified herein, possess the chemical and physiological properties equivalent to the described compounds and which are therefore within the definition of the present invention. Specific attention should be paid to the pharmacology of such compounds in humans, including their interactions with colonic flora.

The preferred compound for use in the present invention is the N-acyl sarcosine conjugate of cholic acid (cholylsarcosine). Sarcosine has the formula $H_3C \cdot NH \cdot CH_2 \cdot COOH$; the structure of cholic acid is complex and is presented in Rawn, Biochemistry. at FIG. 19.2 (1983). Cholylsarcosine is well transported by the ileum and liver and resists bacterial degradation (both deconjugation and dehydroxylation) during intestinal transit, as illustrated in FIG. 2.

In vitro, using an assay for lipase, cholylsarcosine promotes rapid hydrolysis of triglyceride when colipase is present; thus, cholylsarcosine appears to form a ternary complex at the oil/water interface with lipase and colipase in the same manner as the natural bile acid salt, cholyltaurine.

Figure 2:
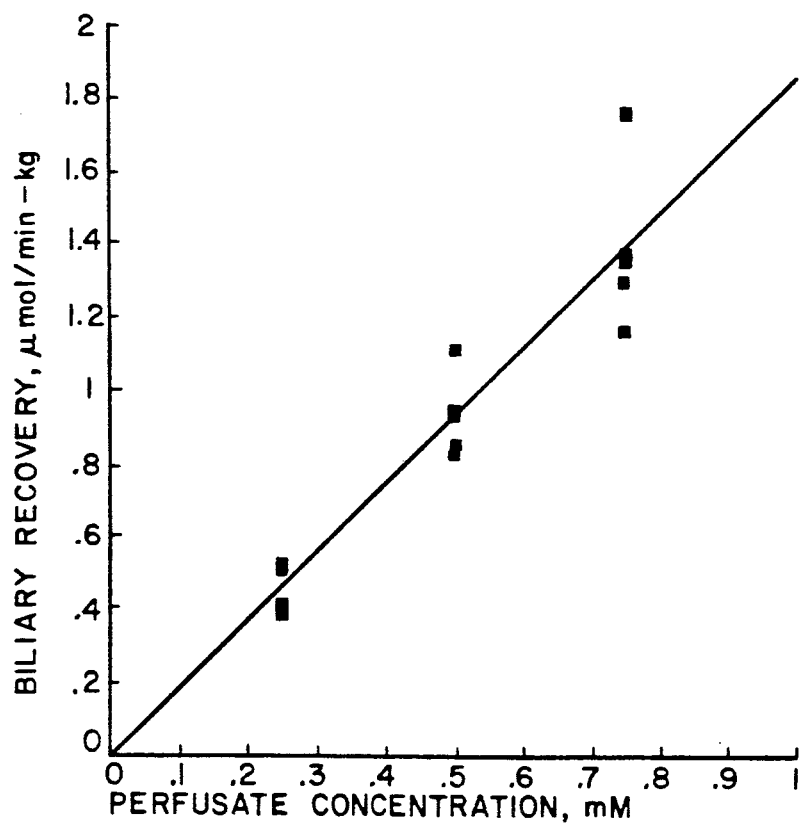
FIG. 2 is a graph showing ileal transport of cholylsarcosine in the anesthetized biliary fistula rat.

Cholylsarcosine is not hepatotoxic, and is well transported by the rat liver and perfused rat ileum, as illustrated in FIGS. 1 and 2. FIG. 1 shows the hepatic transport of cholylsarcosine in the anesthetized biliary fistula rat. Cholylsarcosine was administered intravenously at progressively increasing rates. The T (maximum biliary recovery) is about 20 $\mu$mol/min-kg which is similar to that of cholyltaurine, and indicates that cholylsarcosine is well transported by the rat liver. FIG. 2 illustrates the ileal transport of cholylsarcosine in the anesthetized biliary fistula rat. Cholylsarcosine was infused into the distal intestine at various concentrations. At a concentration up to 0.7 mM, cholylsarcosine is efficiently transported. With chronic feeding in the rat, cholylsarcosine became 30% of the circulating bile acids, confirming its conservation by enterohepatic cycling.

Figure 3:
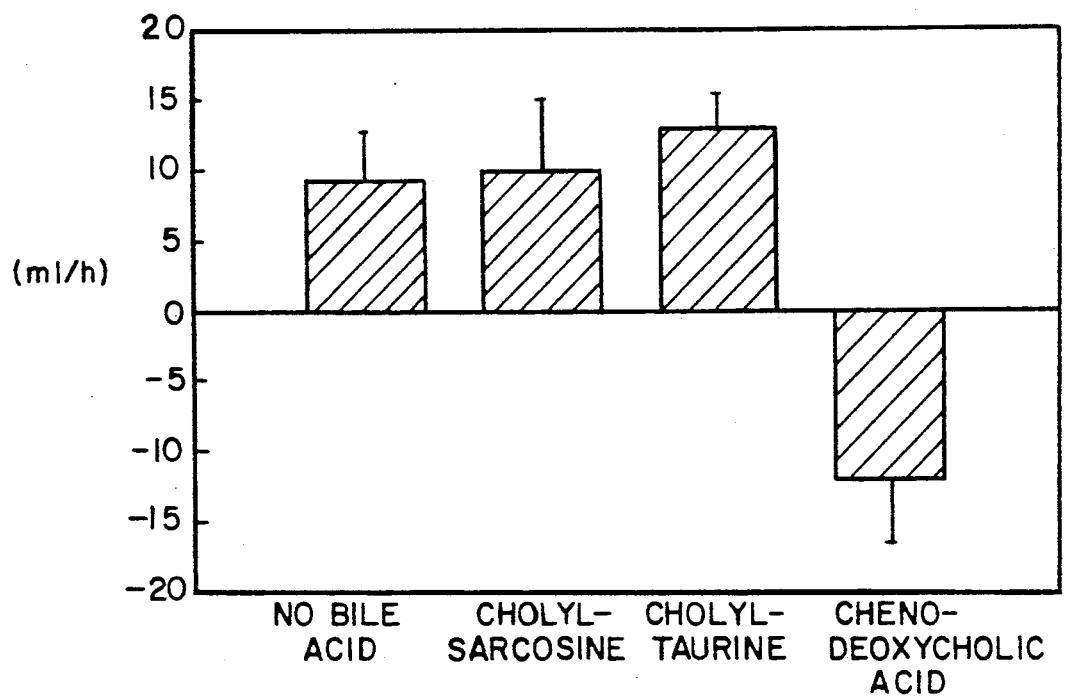
FIG. 3 is a graph showing the effect of cholylsarcosine on water absorption by the perfused colon in the anesthetized rabbit.
Figure 4:
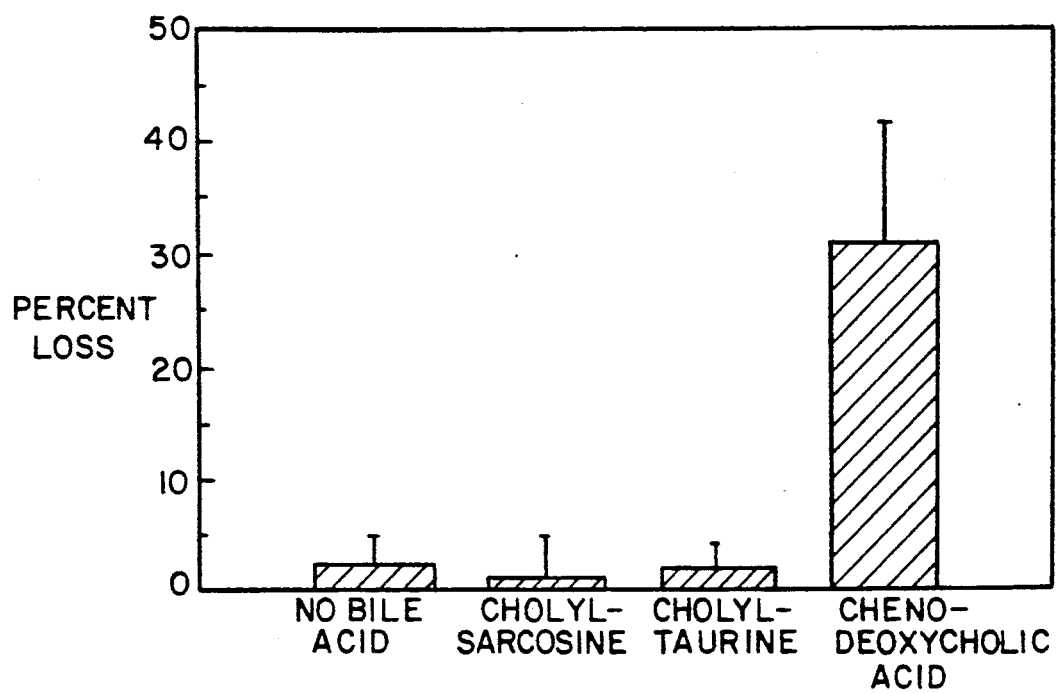
FIG. 4 is a graph showing the effect of cholylsarcosine on erythritol permeability of the perfused colon in the anesthetized rabbit.

Cholylsarcosine does not induce secretion by the perfused rabbit colon, nor increase colonic permeability to erythritol, when compared to chenodeoxycholic acid. Its properties are identical to those of cholyltaurine, as illustrated in FIGS. 3 and 4. FIG. 3 shows the effect of cholylsarcosine on water absorption by the perfused colon in the anesthetized rabbit. A bile acid solution (5 mM) containing a polymeric dye as nonabsorbable marker was perfused. A control period without bile acid preceded the bile acid perfusions. Each solution was perfused over 1 hour and the entire experiment took 4 hours. Chenodeoxycholic acid was always the last bile acid to be perfused. FIG. 4 is a similar graph showing the effect of cholylsarcosine on erythritol permeability of the perfused colon in the anesthetized rabbit. Cholylsarcosine, just as cholyltaurine, causes no increase in erythritol permeability. In contrast, chenodeoxycholate causes a rapid increase in erythritol permeability.

Figure 5:
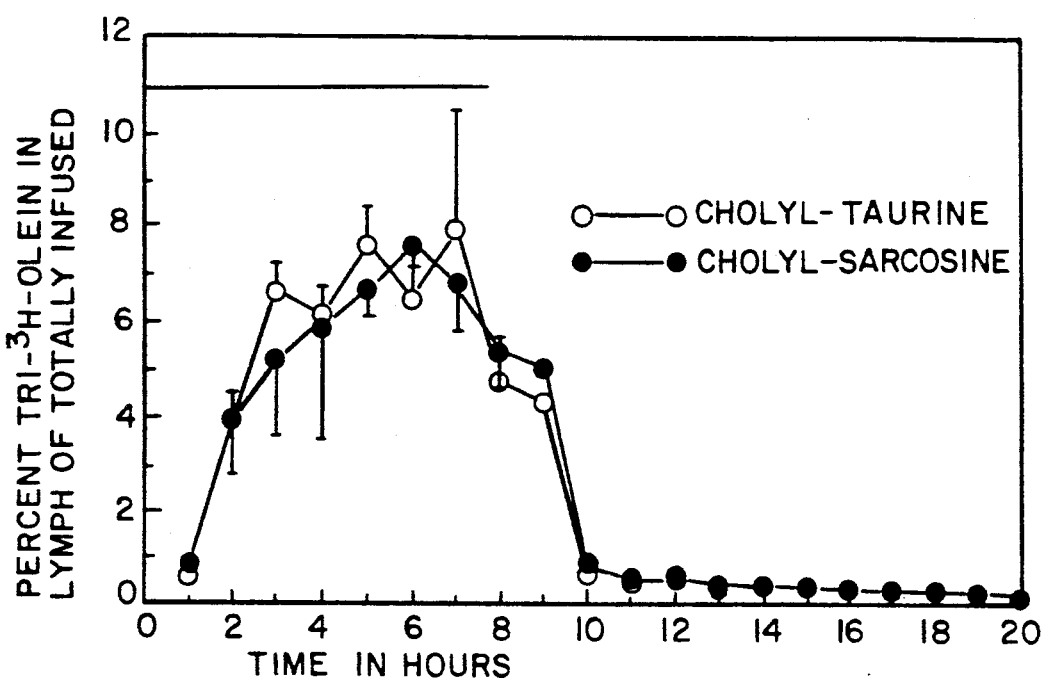
FIG. 5 is a graph showing the rate of absorption of H-triolein in the unanesthetized lymph fistula rat, as promoted by cholylsarcosine or cholyltaurine.
Figure 6:
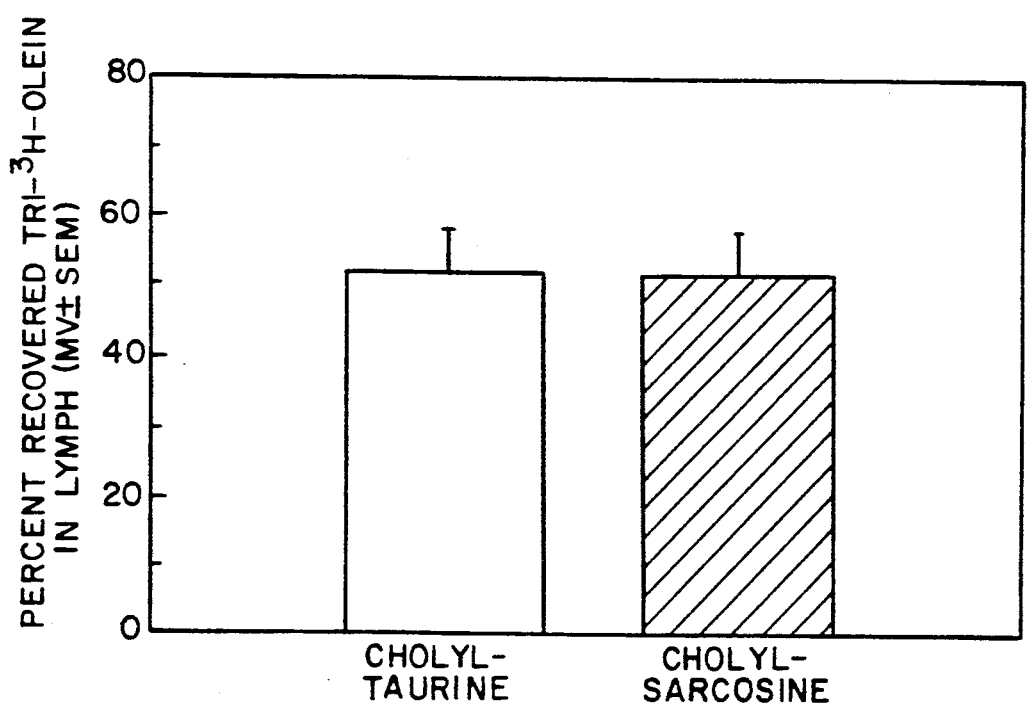
FIG. 6 is a graph showing total recovery of $^3$H-triolein in thoricic duct lymph using cholylsarcosine or cholyltaurine as surfactant.

In vivo, using the perfused rat intestine, cholylsarcosine facilitates the absorption of perfused triglyceride just as well as does cholyltaurine, as shown by the data of FIGS. 5 and 6. In FIG. 5 is shown the rate of absorption of $^3$H-triolein in the unanesthetized lymph fistula rat, as promoted by cholylsarcosine or cholyltaurine. Rats with lymph and bile fistulae, as well as a duodenal catheter, were infused with a solution of 5 mmol/L $^3$H-triolein and 15 mmol/L cholyltaurine or cholylsarcosine for 8 hours. Lymph was collected for 20 hours from the start of the infusion. After surgery, the animals were allowed to recover until the following morning, when infusion with one of the bile acid solutions was begun. The solution containing the other bile acid was infused the following (third) day. Similarly, FIG. 6 illustrates the total recovery of $^3$H-triolein in thoracic duct lymph using cholylsarcosine or cholyltaurine as surfactant. The same experimental conditions were used as in FIG. 5.

The required dosage for successful replacement is expected to be on the order of 12-18 g/day, administered as 4-6 g/meal. The treatment method is preferably performed by encapsulating the medication as, for example, forming capsules containing 500 mg of cholylsarcosine. The patient would take sufficient capsules to obtain the prescribed dose before and during means. The capsule must disperse, yet remain insoluble, in the stomach and be discharged simultaneously with gastric contents.

Potential clinical uses of the compounds of this invention, including cholylsarcosine, as bile acid replacements, include use when bile acid secretion into the small intestine is decreased or when normally secreted bile acids are deconjugated by bacterial overgrowth. Decreased bile acid secretion is found in patients with ileal resection or dysfunction or with biliary fistula, while increased bacterial deconjugation occurs in patients with a blind loop syndrome. Efficacy of cholylsarcosine will be indicated by decreased steatorrhea (increased efficiency of fat assimilation) and by decreased diarrhea (to the extent that it is caused by steatorrhea).

compounds of the present invention, including cholylsarcosine, are anticipated to have a second use, in that their chronic administration will result in enrichment in the circulating bile acids in cholylsarcosine. Bile acid hydrophilicity is a key determinant of bile acid hepatotoxicity and feedback regulation of bile acid biosynthesis. Hydrophilicity may be estimated at least approximately by measuring the relative retention time during reverse phase partition chromatography.

Administration of the compounds of this invention, including cholylsarcosine, should increase the hydrophilicity of the circulating bile acids. Increasing the hydrophilicity of the circulating bile acids by ursodeoxycholic acid (ursodiol) has been shown to desaturate bile in cholesterol and induce cholesterol gallstone dissolution. If cholylsarcosine desaturates bile, it should also induce cholesterol gallstone dissolution.

In addition, recent experiments have shown that increasing hydrophilicity of the bile acid pool by chronic ursodiol administration causes symptomatic improvement and improvement in abnormal liver tests in patients with chronic cholestatic or inflammatory liver disease. It is possible that cholylsarcosine will have similar properties.

It will be recognized by those skilled in the art that there are numerous embodiments of this invention which, while not expressly set forth above, are clearly within the scope and spirit of the invention. The above descriptions are therefore intended to be exemplary only, and the scope of the invention is to be determined solely by the appended claims.

I claim:

1. A method for the replacement of bile acid in the biliary tract during conditions of bile acid deficiency which comprises administering an effective amount of an orally ingestible dosage, one which is and remains insoluble in the stomach, is not enteric coated, and is dispersible in the gastric contents, without being retained in the stomach, and is discharged with the gastric contents a synthetic bile acid comprising a non-deconjugatable reaction product of a natural bile acid and an N-alkyl amino acid or acid analogue.

2. A method as in claim 1 wherein said N-alkyl amino acid is an N-alkyl glycine.

3. A method as in claim 2 wherein said N-alkyl glycine is N-methyl glycine.

4. A method as in claim 1 wherein said natural bile acid is cholic acid.

5. A method as in claim 4 wherein said N-alkyl amino acid is an N-alkyl glycine.

6. A method as in claim 5 wherein said N-alkyl glycine is N-methyl glycine.

7. A bile acid replacement composition which comprises an orally ingestible dosage, one which is and remains insoluble in the stomach, is not enteric coated, and is dispersible in the gastric contents, without being retained in the stomach, and is discharged with the gastric contents the reaction product of a natural bile acid and an N-alkyl amino acid.

8. A composition as in claim 7 wherein said N-alkyl amino acid is an N-alkyl glycine.

9. A composition as in claim 8 wherein said N-alkyl glycine is N-methyl glycine.

10. A composition as in claim 7 wherein said natural bile acid is cholic acid.

11. A composition as in claim 10 wherein said N-methyl amino acid is an N-alkyl glycine.

12. A composition as in claim 11 wherein said N-alkyl glycine is N-methyl glycine.

13. A method for the replacement of bile acid in the biliary tract during conditions of bile acid deficiency which comprises administering and effective amount of an orally ingestible dosage, one which is and remains insoluble in the stomach, is not enteric coated and is dispersible in the gastric contents, without being retained in the stomach, and is discharged with the gastric contents of a synthetic bile acid comprising the non-deconjugatable reaction product of a natural bile acid and an N-alkyl amino acid or acid analogue, wherein by said reaction a side chain of said bile acid is modified to impart to said reaction product the ability to resist bacterial hydrolysis and thereby resist bacterial deconjugation.

14. A method as in claim 13 wherein said modification comprises conjugation with an uncommon amino acid or amino acid analogue, replacement of the peptide bond by a hydrolysis resistant bond or replacement by an amino acid containing bulky groups close to the peptide bond which inhibit hydrolysis.

15. A method as in claim 14 wherein said uncommon amino acid is a d-amino acid, β-analine or n-acetyl glycine.

16. A method as in claim 14 wherein said replacement of said peptide bond comprises formation of an ether bond or an "inverse" peptide bond in which the amino group is on the bile acid and the carboxyl group is on the amino acid.

17. A method as in claim 13 wherein said N-alkyl amino acid or acid analogue is an N-alkyl glycine.

18. A method as in claim 17 wherein said N-alkyl glycine is N-methyl glycine

19. A method as in claim 13 wherein said natural bile acid is cholic acid.

20. A method as in claim 19 wherein said N-alkyl amino acid or acid analogue is an N-alkyl glycine.

21. A method as in claim 20 wherein said N-alkyl glycine is N-methyl glycine.

22. A composition for the replacement of bile acid in the biliary tract during conditions of bile acid deficiency which comprises an orally ingestible dosage, one which is and remains insoluble in the stomach, is not enteric coated, and is dispersible in the gastric contents, without being retained in the stomach, and is discharged with the gastric contents of non-deconjugatable reaction product of a natural bile acid and an N-alkyl amino acid or acid analogue, wherein by said reaction a side chain of said bile acid is modified to impart to said reaction product the ability to resist bacterial hydrolysis and thereby resist bacterial deconjugation.

23. A composition as in claim 22 wherein said modified side chain is formed by conjugation with an uncommon amino acid or amino acid analogue, replacement of the peptide bond by a hydrolysis resistant bond or replacement by an amino acid containing bulky groups close to the peptide bond which inhibit hydrolysis.

24. A composition as in claim 23 wherein said uncommon amino acid is a d-amino acid, B-analine or n-acetyl glycine.

25. A composition as in claim 23 wherein said replacement of said peptide bond comprises formation of an ether bond or an "inverse" peptide bond in which the amino group is on the bile acid and the carboxyl group is on the amino acid.

26. A composition as in claim 22 wherein said N-alkyl amino acid or acid analogue is an N-alkyl glycine.

27. A composition as in claim 26 wherein said N-alkyl glycine is N-methyl glycine.

28. A composition as in claim 22 wherein said natural bile acid is cholic acid.

29. A composition as in claim 28 wherein said N-alkyl amino acid or acid analogue is an N-alkyl glycine.

30. A composition as in claim 29 wherein said N-alkyl glycine is N-methyl glycine.

31. A composition according to claim 1 wherein said dosage is administered in an encapsulated form.

32. A composition according to claim 7 wherein said dosage is administered in an encapsulated form.

33. A method according to claim 13 wherein said dosage is administered in an encapsulated form.

34. A method according to claim 22 wherein said dosage is administered in an encapsulated form.

* * * * *

UNITED STATES PATENT AND TRADEMARK OFFICE
CERTIFICATE OF CORRECTION

PATENT NO. : 5,079,240

DATED : January 7, 1992

INVENTOR(S) : Alan F. Hofmann

It is certified that error appears in the above-identified patent and that said Letters Patent is hereby corrected as shown below:

Column 8, Line 26 "B-analine" should read --$\beta$-analine--.

Signed and Sealed this

Fifth Day of October, 1993

*Attest:*

BRUCE LEHMAN

*Attesting Officer*      *Commissioner of Patents and Trademarks*